(12) United States Patent
Kast et al.

(10) Patent No.: US 8,401,648 B2
(45) Date of Patent: Mar. 19, 2013

(54) HOUSING FOR IMPLANTABLE MEDICAL DEVICE

(75) Inventors: John E. Kast, Hugo, MN (US);
Reginald D. Robinson, Plymouth, MN (US); Randy S. Roles, Elk River, MN (US); Bernard Q. Li, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 897 days.

(21) Appl. No.: 12/186,855

(22) Filed: Aug. 6, 2008

(65) Prior Publication Data
US 2008/0294207 A1    Nov. 27, 2008

Related U.S. Application Data

(63) Continuation-in-part of application No. 11/590,250, filed on Oct. 31, 2006.

(51) Int. Cl.
*A61N 1/375* (2006.01)
(52) U.S. Cl. ......................................................... 607/36
(58) Field of Classification Search ................ 607/36–37
See application file for complete search history.

(56) References Cited

U.S. PATENT DOCUMENTS

| | | | |
|---|---|---|---|
| 5,876,424 A * | 3/1999 | O'Phelan et al. | 607/36 |
| 5,902,326 A * | 5/1999 | Lessar et al. | 607/36 |
| 6,010,803 A | 1/2000 | Heller, Jr. | |
| 6,360,749 B1 | 3/2002 | Jayaraman | |
| 6,500,187 B1 | 12/2002 | Petersen | |
| 6,505,073 B2 | 1/2003 | Gramse | |
| 6,800,326 B1 | 10/2004 | Uchiyama | |
| 7,123,966 B2 * | 10/2006 | Deininger et al. | 607/36 |
| 7,212,864 B2 * | 5/2007 | Wahlstrand et al. | 607/36 |
| 7,263,401 B2 | 8/2007 | Scott | |
| 2003/0120320 A1* | 6/2003 | Solom | 607/36 |
| 2007/0233195 A1 | 10/2007 | Wahlstrand | |
| 2008/0021511 A1 | 1/2008 | Scott | |
| 2008/0103543 A1 | 5/2008 | Li | |
| 2008/0269829 A1 | 10/2008 | Li | |

* cited by examiner

*Primary Examiner* — Scott Getzow
*Assistant Examiner* — Amanda Patton

(57) ABSTRACT

An implantable medical device includes a housing having frame with one or more openings. The openings of the frame are covered with a thin metallic foil that is welded to the frame to provide a hermetic seal. Non-conductive members may be placed in or about the openings to provide a backing or structural support for the metallic foil. By decreasing the mass of conductive material capable of forming eddy currents, improved recharge or telemetry performance may be realized.

18 Claims, 10 Drawing Sheets

HOUSING FOR IMPLANTABLE MEDICAL DEVICE

RELATED APPLICATIONS

This application is a continuation-in-part application of U.S. patent application Ser. No. 11/590,250, filed Oct. 31, 2006, published on May 1, 2008 as U.S. application Ser. No. 2008/0103556, which application is hereby incorporated herein by reference in its entirety to the extent that it does not conflict with the disclosure presented herein.

FIELD

The present disclosure relates to implantable medial devices. In particular, this disclosure relates to an implantable medical device housing having an opening covered by a thin metallic foil or by a non-conductive transparent single crystal material.

BACKGROUND

Implantable medical devices are used to produce therapeutic results in a patient or for monitoring physiologic parameters of a patient. Examples of IMDs include implantable drug infusion pumps, implantable neurostimulators, implantable cardiovertor defibrillators, implantable cardiac pacemakers, and cochlear implants. Most of these IMDs either provide an electrical output or contain electrical circuitry to perform their intended functions. These devices are typically powered by a battery contained within the housing of the implantable medical device.

As the useful life of an implantable medical device is dependent upon the operating life of the battery that provides power, the development of rechargeable power sources that can be charged using electromagnetic energy from outside the patient's body provides the opportunity for longer life implantable medical devices. The ability to deliver electromagnetic energy to the charging circuitry within the implantable medical device is affected by the electrical characteristics of the housing of the implantable medical device. Typically, implantable medical device housings are made of a biocompatible metal such as commercial pure titanium. It has been suggested to employ a housing formed of a material having a higher resistivity than conventional commercial pure titanium to improve electrical performance of the recharging circuitry. During the recharge process, eddy currents can form in the housing due to the electromagnetic energy transmitted to recharge the battery. Because the eddy currents heat the housing, the amount of energy transferred to recharge is limited to prevent excessive heating of the device, resulting in relatively slow recharging of the battery. By employing a higher resistivity housing, the amount of energy that may be employed to recharge the device may be increased, and thus may shorten the time to recharge the device. A higher resistivity housing would also enhance telemetry to and from the implantable medical device, and would reduce magnetic resonance imaging (MRI) heating effects when a patient with an implantable medical device is subjected to an MRI procedure.

Decreasing the mass of conductive material in which eddy currents may be formed may also serve to improve the recharge and telemetry performance of an implantable medical device or reduce MRI-induced heating. However, problems may arise with housings that are too thin, as the structural integrity may be weakened and the ability to maintain a hermetic seal may be compromised.

BRIEF SUMMARY

The present disclosure provides an implantable medical device with a housing having frame with one or more openings. The openings of the frame are covered with a thin metallic foil that is joined to the frame to provide a hermetic seal; e.g., by welding. Alternatively or in addition, the openings of the frame may be covered by thin sections of transparent single-crystal material which may be anodically-bonded to the frame. Non-conductive members may be placed in or about the openings to provide a backing or structural support for the metallic foil. By decreasing the mass of conductive material capable of forming eddy currents, improved recharge or telemetry performance may be realized.

In an embodiment, the disclosure describes an implantable medical device that includes a housing having a welding frame. The welding frame includes an opening. The housing further includes a metallic foil covering the opening and welded to the frame to hermetically seal the housing.

In an embodiment, the disclosure describes a method for forming a hermetically sealed housing of an implantable medical device. The method includes welding a metallic foil to a frame of the housing. The frame has an opening, and the foil hermetically seals the opening when welded to the frame.

The advantages of the devices, housings, and methods described herein will be readily understood from the following detailed description when read in conjunction with the accompanying drawings.

Figure 1:
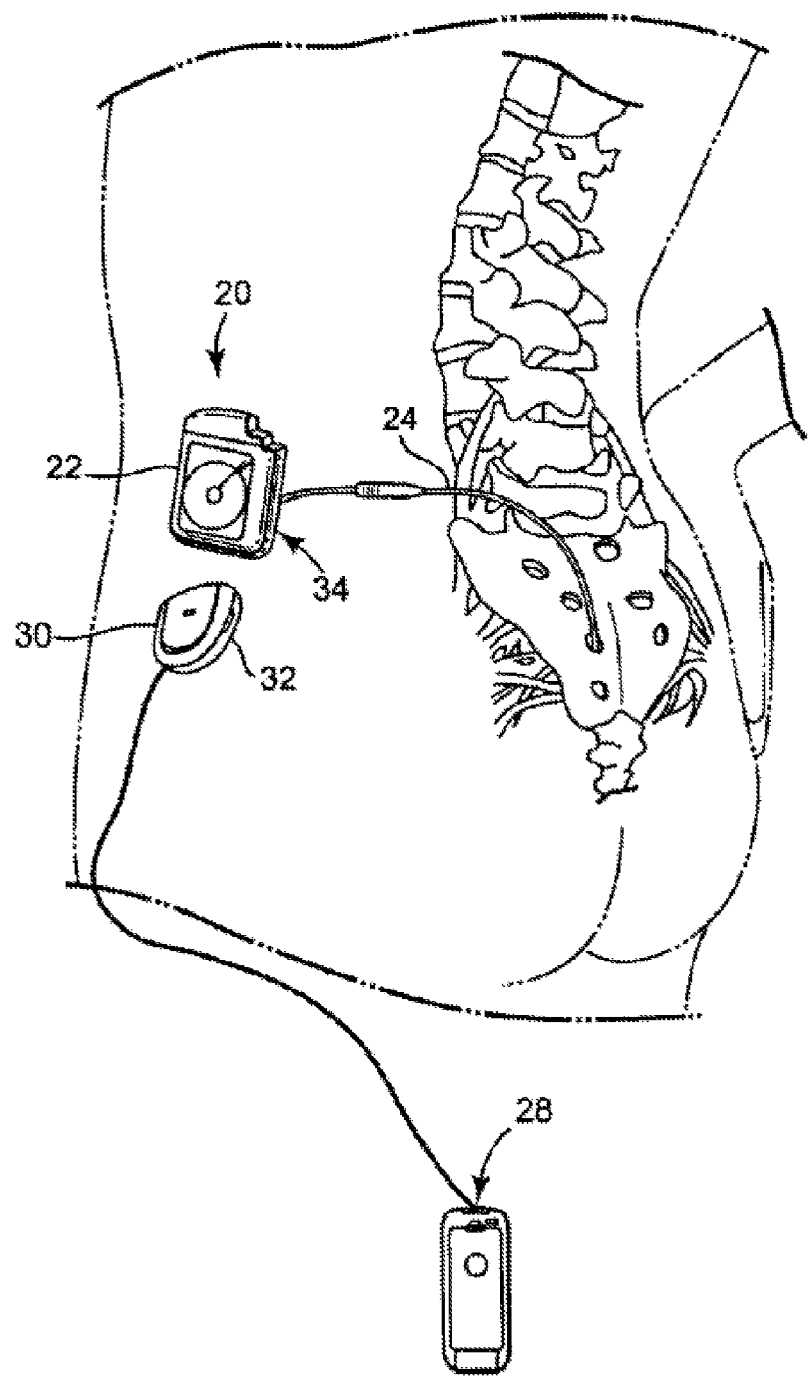
FIG. 1 is a schematic diagram showing a representative implantable medical device and associated external device in an environment of a patient.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

As used herein, "non-conductive material" is a material having a conductance of less than about $10^{-4}$ Seimens/cm. For example, materials having a conductance of less than about $10^{-8}$ Seimens/cm are generally considered insulators. Examples of non-conductive materials include glass, ceramic, injection molded polymers such as LCP, polysulfone, PEEK or liquid silicone rubber (LSR)

The present disclosure describes, inter alia, an implantable medical device with a housing having frame with one or more openings. The openings of the frame are covered with a thin metallic foil that is welded to the frame to provide a hermetic seal. Non-conductive members may be placed in or about the openings to provide a backing or structural support for the metallic foil. By decreasing the mass of conductive material capable of forming eddy currents, improved recharge or telemetry performance may be realized.

Nearly any implantable medical device or system having a housing can be adapted for use with housings as described herein. For example, hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; infusion devices; or the like may be adapted for use with housings as described herein. Such devices may include associated devices, such as leads or catheters to deliver therapy, perform monitoring functions, or the like, at locations removed from the device having a housing as described herein.

Referring to FIG. 1, a rechargeable implantable medical device 20 is shown implanted in a patient. An implantable electrical signal generator 22 is shown in FIG. 1, but other embodiments such as drug delivery pumps, pacemakers, defibrillators, diagnostic recorders, cochlear implants, or the like are also applicable. Implantable medical devices 20 are often implanted subcutaneously approximately one centimeter below the surface of the skin with an associated therapy delivery element, such as an electrical lead 24 or catheter, extending to one or more therapy sites. Of course, device 20 may be implanted in any suitable location of the patient. The implantable medical device 20 may be recharged with a recharging device 28 such as a patient charger or programmer that also has a charging capability.

Recharging an implantable medical device 20 may begin with placing a recharging head 30 containing a primary recharging coil 32 against the patient's skin near the proximal side of the medical device 20. Some rechargers 28 have an antenna locator that indicates when recharge head 30 is aligned closely enough with implanted medical device 20 for adequate inductive charge coupling. The recharge power transfer signal is typically a frequency that will penetrate transcutaneously to the location of implanted medical device 20 such as a frequency in the range from 5.0 KHz to 100 KHz. The power transfer signal may be converted by implantable medical device 20 into regulated DC power that may be used to charge a rechargeable power source 34. In some embodiments, telemetry may also be conducted between the recharger 28 and the implanted medical device 20 during recharging. Telemetry may be used to aid in aligning recharger 28 with the implanted medical device 20, and telemetry may be used to manage the recharging process. Telemetry is typically conducted at a frequency in the range from 150 KHz to 200 KHz using a medical device telemetry protocol, but may also include Bluetooth®, 802.11, and Medical Implant Communication Service (MICS) frequency band communication. For telemetry, the recharger 28 and implanted medical device 20 typically have a separate telemetry coil. Although, the recharging coil can be multiplexed to also serve as a telemetry coil.

While device 20 shown in FIG. 1 is rechargeable, it will be understood that the teachings presented herein apply to devices 20 that are not rechargeable.

Figure 2:
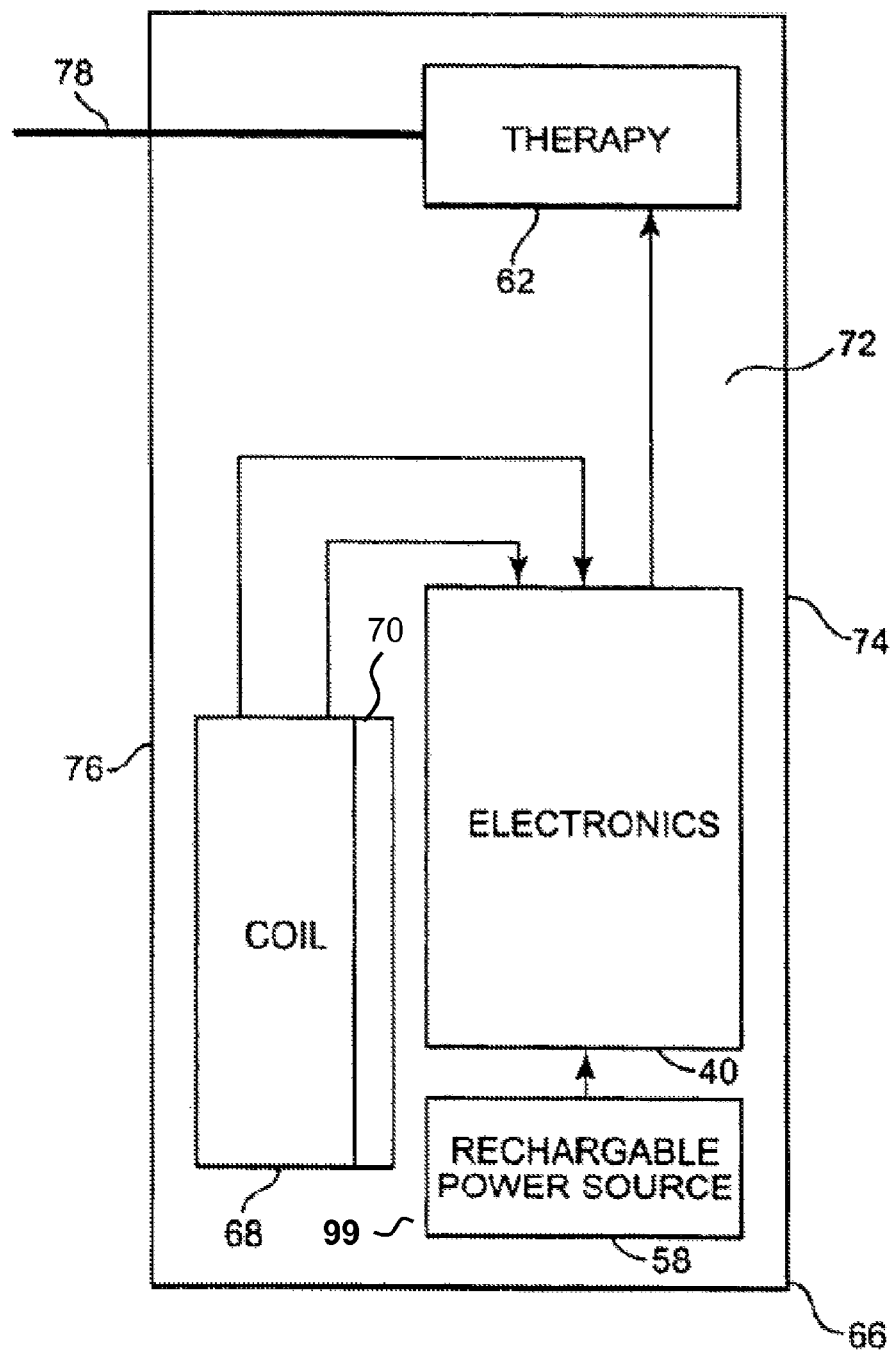
FIG. 2 is a schematic block diagram of a representative implantable medical device.

Referring to FIG. 2, a schematic diagram of a rechargeable implantable medical device 20 is shown in block form. The depicted implantable medical device 20 includes a housing 66, electronics 40, a rechargeable power source 58, and a secondary recharging coil 68, and a magnetic shield 70. Housing 66, in the depicted embodiment, has an interior cavity 72, an exterior surface 74, a proximal face 76, and a therapy connection 78. The therapy connection 78 can be any type of therapy connection 78 such as a stimulation feedthrough, a drug infusion port, or a physiological sensor feedthrough. There can also be more than one therapy connection 78 and a combination of different types of therapy connections 78. Housing 66 is preferably hermetically sealed.

Electronics 40 are carried in the housing interior cavity 72 and configured to perform a medical therapy or diagnostic. The depicted electronics 40 are operably coupled therapy module 62, and secondary recharge coil 68. Power source 58 is carried in the housing interior cavity 72 and coupled to electronics 40. Power source 58 can be a physical power source such as a spring, an electrical power source such as a capacitor, a chemical power source such as a battery, or the like. The battery may be a rechargeable battery lithium ion (Li+) battery or the like.

The secondary recharging coil 68 may be coupled to the electronics 40 and may also be coupled to the rechargeable power source 58 in addition to the electronics 40. The secondary recharging coil 68 may be manufactured from any suitable material with desirable electromagnetic properties such as copper wire, copper magnet wire, copper litz, woven wire, gold alloy or the like. The secondary recharging coil 68 may be manufactured from a wide variety of sizes such as wire diameters in the range from about 0.016 cm (34 AWG, American Wire Gauge) to about 0.40 cm (26 AWG), or any other suitable diameter.

Figure 3:
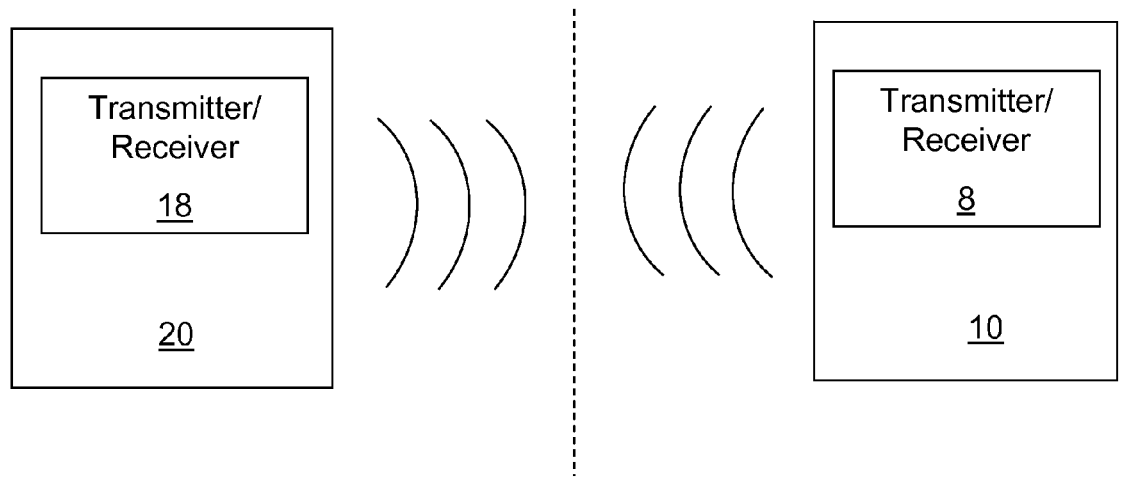
FIG. 3 is a schematic block diagram of representative internal and external devices communicating with each other.

Referring to FIG. 3, an external device 10 in wireless communication with implantable device 20 is shown. External device 10 may communicate with implantable device 20 through patient's skin, which is represented by the dashed line in FIG. 4. In various embodiments, where implantable device 20 is a programmable device, external device 10 may be a programmer device, such as Medtronic Inc.'s N'Vision™ clinician programmer. Of course external device 10 may be any device capable of wirelessly communicating with implantable device 20, such as a patient programmer, a computer, a personal data assistant, or the like. As shown in FIG. 3, implantable device 20 may contain a wireless transmitter or receiver 18, and external device 10 may contain a wireless transmitter or receiver 8 to allow implantable device 20 and external device 10 to communicate. External device 10 and implantable device 20 may be capable of one-way (external device 40 to implantable device 20 or implantable device 20 to external device 40) or two-way communication.

Figure 4:
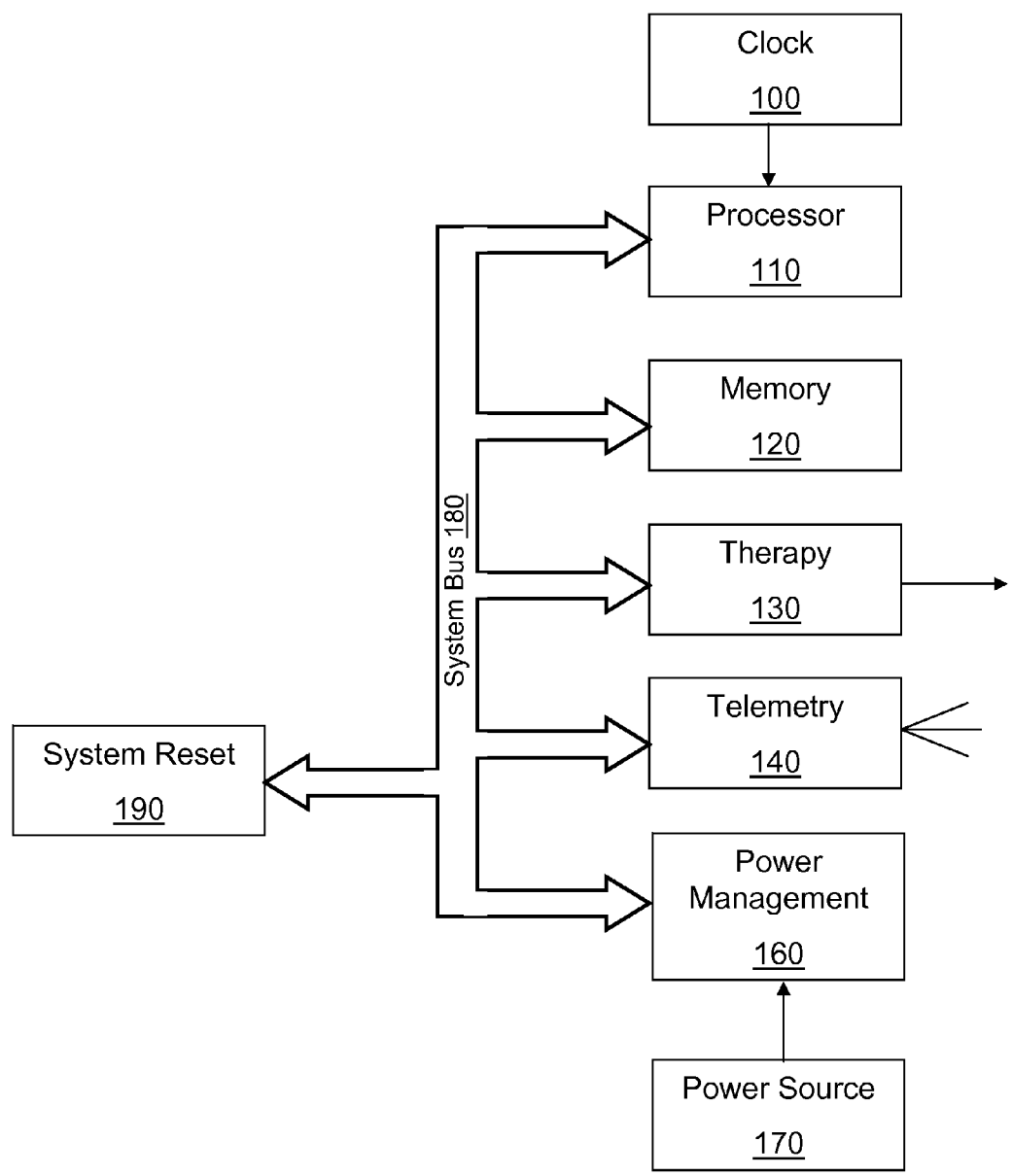
FIG. 4 is a schematic block diagram of a representative implantable medical device.
Figure 5A:
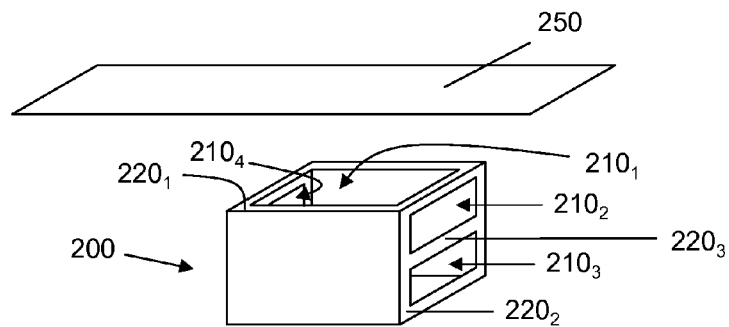
FIGS. 5A-D are schematic perspective views of representative housings and associated components thereof.
Figure 5B:
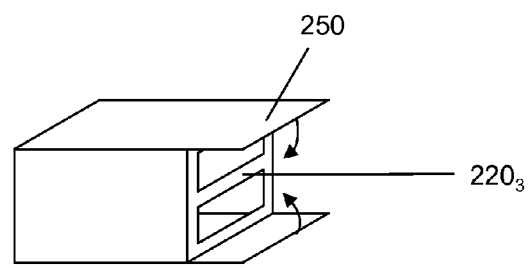
Figure 5C:
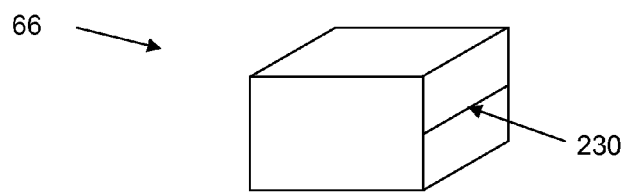
Figure 5D:
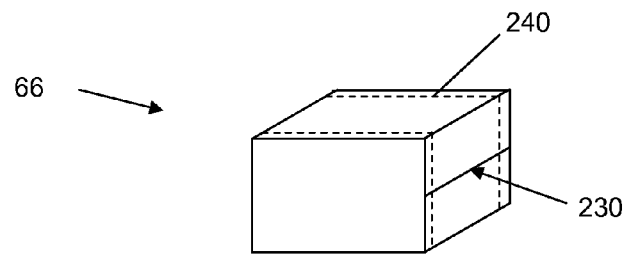

Referring to FIG. 4, some representative electronic components of an implantable medical device 20, such as a therapy delivery device, according to various embodiments are shown in block form. Device 20 as depicted in the embodiment shown in FIG. 4 includes a clock 100, a processor 110, a memory 120, a therapy output or delivery component 130, a telemetry component 140, a sensor 150, a power management module 160, a power source 170, an alert module 185, and a system reset module 190. Other components of active implantable medical device 20 can include, e.g., a diagnostics module (not shown). In various embodiments, all components except the power source 170 are configured on one or more Application Specific Integrated Circuits (ASICs) or are one or more discrete components. In various embodiments, all components except the clock and power source are connected to bi-directional data bus 180 that is non-multiplexed with separate address and data lines.

Telemetry 140 module or other wireless module provides for communication between implantable device 20 and external device 40 such as a programmer. Communication may be bi-directional. Telemetry module 140 generally includes a telemetry antenna, a receiver 18 (see, e.g., FIG. 3), a transmitter 48 (see, e.g., FIG. 3), and a telemetry processor. Telemetry modules are generally known in the art and are further detailed in U.S. Pat. No. 5,752,977, entitled "Efficient High Data Rate Telemetry Format For Implanted Medical Device" issued to Grevious et al. (May 19, 1998). While module 140 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Therapy module 130 refers to components for carrying out the delivery or generation of therapeutic output to be delivered to a patient from active device 20. One of skill in the art will appreciate that the components may vary on a device-by-device basis and a therapy-by-therapy basis. For example, therapy module 130 may contain an oscillator if device 20 is an electrical signal generator and may contain a pumping mechanism if device 20 is an infusion device.

While not shown in FIG. 4, device 20 may include a recharge module; e.g. as depicted in FIG. 2. It will be understood that the components described in FIGS. 1-4 are but examples of components that an implantable device 20 may have and that many other device or system configurations may be employed to in accordance with the teachings presented herein.

Referring now to FIGS. 5-11, representative examples of housings 66, or components thereof, for implantable medical devices are shown. As shown in FIGS. 5A-D, housing 66 includes a frame 200 including one or more openings $210_1$, $210_2$, $210_3$. An opening $210_1$, $210_2$, $210_3$ may be formed by an edge or ridge $220_1$, $220_2$, $220_3$. An edge or ridge $220_1$, $220_2$, $220_3$ of the frame 200 may serve to provide a surface to which a metallic foil 250 or sheet or non-conductive single crystal material may be affixed, such as a welding surface, a surface for adhesion, or the like. As shown in FIGS. 5B-D, a metallic foil or sheet 250 or non-conductive single crystal material is disposed across and covers one or more opening $210_1$, $210_2$, $210_3$ of the frame 200. The sheet 250 may be placed about the frame such that a seam 230 ends on a ridge $220_3$ or surface of the frame 200. The two edges of the seam 230 may be affixed to the ridge $220_3$ or surface by welding, adhesive, fastener, or the like. As shown in FIG. 5D, the sheet 250 may be affixed to the frame at various edges or surfaces (dashed lines indicate an example of where the sheet is affixed to the frame) to seal; e.g. hermetically seal, the interior of the housing 66.

As used herein "foil" and "sheet" are used interchangeably and have meanings typically ascribed to each term. In various embodiments, the foil 250 has a substantially uniform thickness throughout its dimensions. For example, the thickness may not vary more than 30%, more than 20%, or more than 10%, from its average thickness at a given point In numerous embodiments, one or more openings of the frame 200 of the housing 66 that is covered by foil 250 is configured to be aligned with a recharge or telemetry coil of the implantable medical device to allow for improved power coupling efficiency and telemetry distance for the IMD.

The total surface area occupied by the one or more openings 210 of a frame 200, relative to the total surface area of the housing 66, as depicted in FIG. 5 or other figures depicted and described below, in various embodiments, is about 10% or greater; e.g., about 25% or greater, 50% or greater, or 75% or greater. The greater the surface area of the openings relative to the surface area of the housing, the greater the reduction in the mass of the conductive material that may form eddy currents, and thus the greater increase in recharge or telemetry efficiency or reduction in heating associated with MRI procedures.

A frame 200 as depicted in FIG. 5 or other figures depicted and described below may be formed, machined or metal injection molded of any material to which foil 250 may be joined, e.g. via welding. For example, frame may be formed of metallic material, such as a titanium alloy. In various embodiments, the metallic material has a tensile yield strength of greater than about 30 ksi; e.g., greater than about 50 ksi, greater than about 70 ksi, or between about 70 ksi and 150 ksi. In various embodiments the metallic material has a resistivity of greater than about 40 micro-Ohm-centimeter; e.g., greater than about 50 micro-Ohm-centimeter, greater than about 75 micro-Ohm-centimeter, greater than about 100 micro-Ohm-centimeter, or between about 100 micro-Ohm-centimeter and about 210 micro-Ohm-centimeter. For titanium alloys having such properties, see U.S. patent application Ser. No. 11/590,250.

According to various embodiments, a frame is made from a titanium (Ti) alloy having the general formula Ti—Al—B—C where B represents one or more alloy elements such as V, Sn, Mo, Nb, Zr, and combinations thereof and C represents one or more impurity elements such as N, C, H, Fe, O, Si, Pd, Ru, and combinations thereof. Aluminum is provided in an amount between approximately 2 and 7 weight percent according to numerous embodiments. Elements represented by B and C in the above formula may be present in amounts shown in Table 1 according to various embodiments.

TABLE 1

| Element | Approximate Weight Percent |
|---------|---------------------------|
| V | 2-6 |
| Sn | 1.5-6.5 |
| Mo | <6 |
| Nb | <2 |
| Zr | <5 |
| N | <0.05 |
| C | <0.1 |
| H | <0.0015 |
| Fe | <2 |
| O | <0.3 |
| Si | <0.5 |
| Pd | <1 |
| Ru | <0.02 |

According to numerous embodiments, frame 200 is formed from commercial pure Ti Grade 1. According to various embodiments, frame 200 is formed from a titanium alloy having the formula Ti-6Al-4V (referred to as Ti64). Such an alloy has a greater tensile yield strength than commercial pure Ti Grade 1 and also has better power coupling efficiency and improved telemetry distance.

In various embodiments, frame 250 is formed, machined or molded from a titanium alloy having a composition of Ti-4.5Al-3V-2Fe-2Mo-0.15O. One example of such an alloy is commercially available from JFE Steel Corporate of Chiba, Japan under the trade name SP-700. Based on known properties of this alloy, it is believed that such a material will be sufficiently biocompatible to allow its use in implantable medical devices, while also providing enhanced power coupling and recharging efficiency, improved telemetry distance, reduced heating effects during magnetic resonance imaging (MRI), and improved tolerance for compression stress. An additional advantageous feature of the SP-700 alloy is that it has a relatively small grain size that allows it to be superplastically deformed at a relatively low temperature (e.g., approximately 775° C.).

Another suitable alloy is commercially available from Allvac of Albany, Oreg. under the trade name ATI425 and having a composition of Ti-4Al-2.5V-1.5Fe-0.25O. Other suitable titanium alloys include Ti-6Al-2Sn-4Zr-2Mo (Ti6242), Ti-3Al-2.5V (Grade 9), and titanium matrix composites (alpha and near alpha titanium matrix with SiC, TiC, TiO particles distributed therein). In various embodiments, the frame is formed of Ti-8Al-Mo-V (Ti811) alloy, which is not as formable as some of the other specific alloys identified above, but has excellent resistivity values.

While many of the titanium alloys discussed above are alpha or near alpha titanium alloys, it will be understood that any other suitable alloy may be employed, such as beta titanium alloys. Examples of beta alloys include betaC, beta21S, and Ti-15Mo. In various embodiments, the alloys have a resistivity greater than about 115 microOhm-cm. Other alloys that may be employed include titanium alloy/ceramics, such as Ti-6Al-4V/TiC, or the like.

In various embodiments, frame 200 is formed from a process including metal injection molding an initial frame, aksing a portion of the initial frame, etching a portion of the frame to result in a thinner frame portion, and joining thinned frame portions; e.g. as describe in U.S. patent application Ser. No. 11/796,116, entitled "Metal Injection Molded Titanium Alloy Housing for Implantable Medical Devices", filed on Apr. 26, 2007, which application is hereby incorporated herein by reference in its entirety.

Foil 250 may be formed of materials described above with regard to frame 200. Foil 250 may be formed of the same material as, or of a different material than, frame 200. It is desirable for foil 250 to be made of material that is sufficiently formable to be made thin. Formability of the various titanium alloys described above and other titanium alloys is described in U.S. patent application Ser. No. 11/590,250. In various embodiments, foil 250 is less than 0.007 inches thick; e.g., less than 0.06 inches thick or between 0.04 and 0.06 inches thick. Foils thinner than about 0.003 or 0.004 inches thick may not have sufficient structural integrity or may be too difficult to form with many titanium alloys.

In various embodiments, one or more opening of frame is covered with a non-conductive single crystal material. Examples of non-conductive single crystal materials include polycrystalline, piezoceramic or sapphire materials, and the like. Such materials can generally be formed into sheets having a thickness in the range of about 0.025 inches to about 0.065 inches. The non-conductive single crystal sheet may be joined to the frame to form a hermetic seal; e.g. via anodic bonding. A transparent window would result; allowing additional processing via laser, UV, or other radiant energy sources to occur after the cavity was hermetically sealed.

Figure 6A:
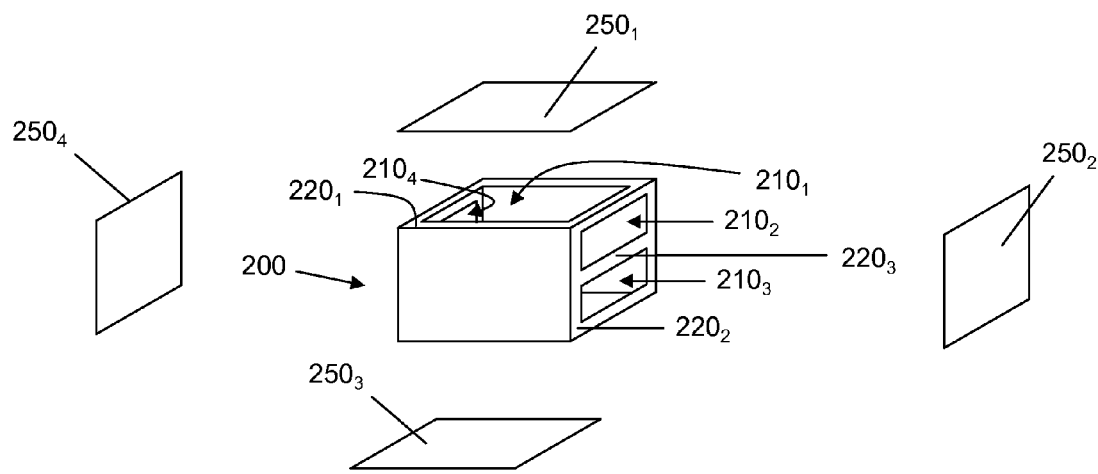
FIGS. 6A-B are schematic perspective views of a representative housing and associated components thereof.
Figure 6B:
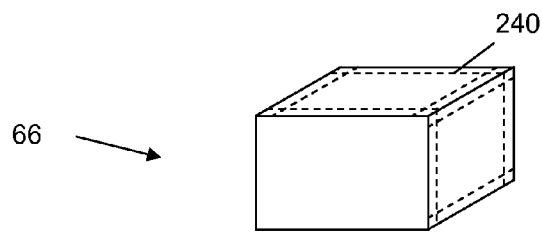

As shown in FIGS. 6A-B, more than one metallic foil sheet $250_1$, $250_2$, $250_3$, $250_4$ or non-conductive single crystal material may be used to cover one or more openings $210_1$, $210_2$, $210_3$ of frame 200. One or more of the sheets $250_1$, $250_2$, $250_3$, $250_4$ may be affixed to an edge of ridge $220_1$, $220_2$, $220_3$ or other surface of the frame 200, as shown by dashed lines in the embodiment depicted in FIG. 6B) to seal the interior of the housing 66.

Figure 7A:
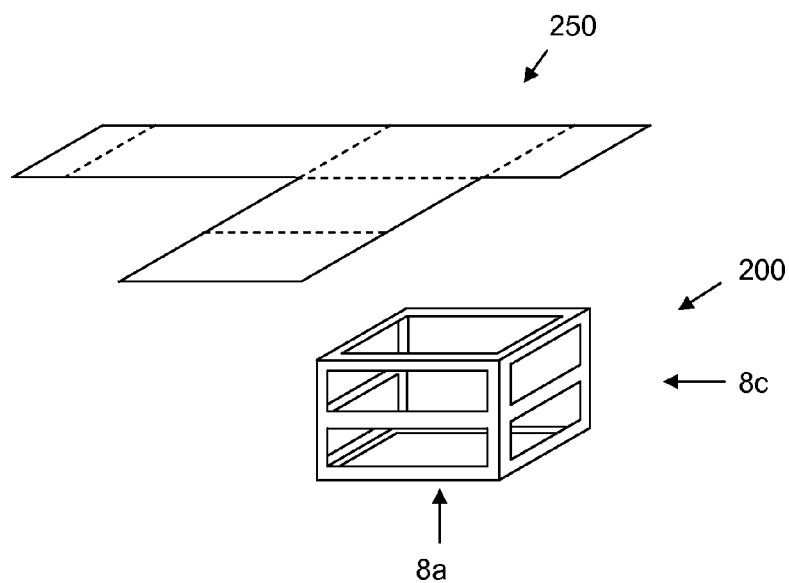
FIGS. 7A-B are schematic perspective views of a representative housing and associated components thereof
Figure 7B:
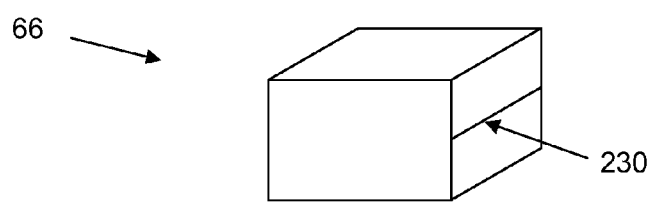

Metallic sheet 250 or non-conductive single crystal material may be formed, cut or otherwise made to any suitable shape. Referring now to FIGS. 7A-B, cube shaped frame 200 includes openings on all six surfaces and a single metallic foil sheet 250 is configured to cover all of the openings. Where sheet 250 forms a seam 230 or overlap when disposed about frame 200, sheet 250 may be affixed to frame 220.

Figure 8A:
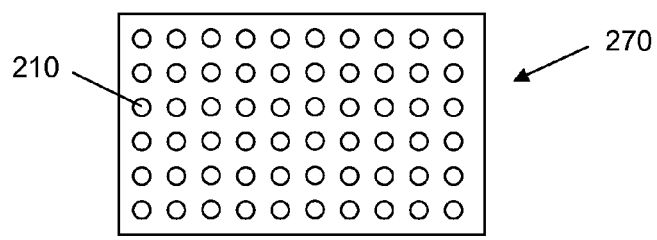
FIGS. 8A-C are schematic head-on views of alternative representative housing walls or surfaces having openings.
Figure 8B:
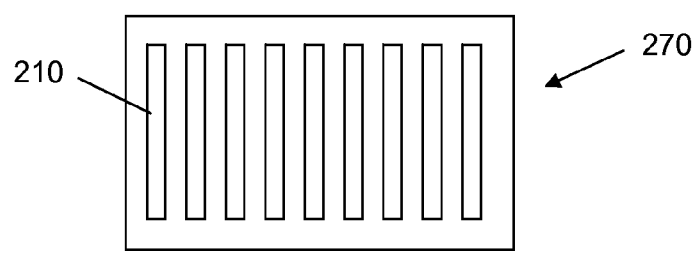
Figure 8C:
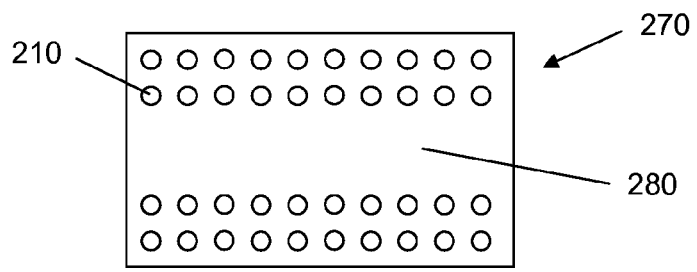

Referring now to FIGS. 8A-C, alternative configurations of walls 270 or surfaces of frames are shown. For example, FIGS. 8A-B depict alternative surfaces of the bottom of frame depicted in FIG. 7A viewed along line 8a-b. FIG. 8C depicts an alternative surface of the side of frame depicted in FIG. 7A viewed along line 8c having a region 280 to which the foil or non-conductive single crystal material may be affixed; e.g., by welding or adhesive. While shown with regard FIG. 7A, the walls 270 or surfaces shown in FIGS. 8A-C may be used with regard to any embodiment depicted or described herein. The walls 270 or surfaces shown in FIGS. 8A-C include one or more openings 210. The openings 210 may be formed by any suitable mechanism, such as by molding, punching, cutting or the like. Such openings 270 may be desirable when the walls 270 or surfaces are formed of metallic material to reduce the overall mass of metallic material used in forming the housing. Walls 270 or surfaces as depicted in FIGS. 8A-C may be formed as a part of the frame or may be affixed to the frame; e.g., via welding, adhesive, fasteners, or the like. If formed of metallic material, the walls 270 or surfaces are preferably formed of material that have a resistivity of greater than about 40 micro-Ohm-centimeter and a tensile yield strength of greater than about 30 ksi. Such materials include those described above as being suitable with regard to foils and frames. Walls 270 or surfaces as depicted in FIGS. 8A-C can serve to reduce the amount of conductive material present in the housing, while providing a structural backing against which the thin foil may rest. Due to the thinness of the foil, it may be desirable to employ a surface or wall 270 as a backing to provide reinforcement for the foil to prevent punctures, tears, cuts, rips or the like.

The walls 270 or surfaces depicted in FIGS. 8A-C may be alternatives to the walls or surfaces depicted in FIGS. 5-7 of the frame or may be affixed to the frame by welding, adhesive, interference or snap fit, or the like.

Figure 9A:
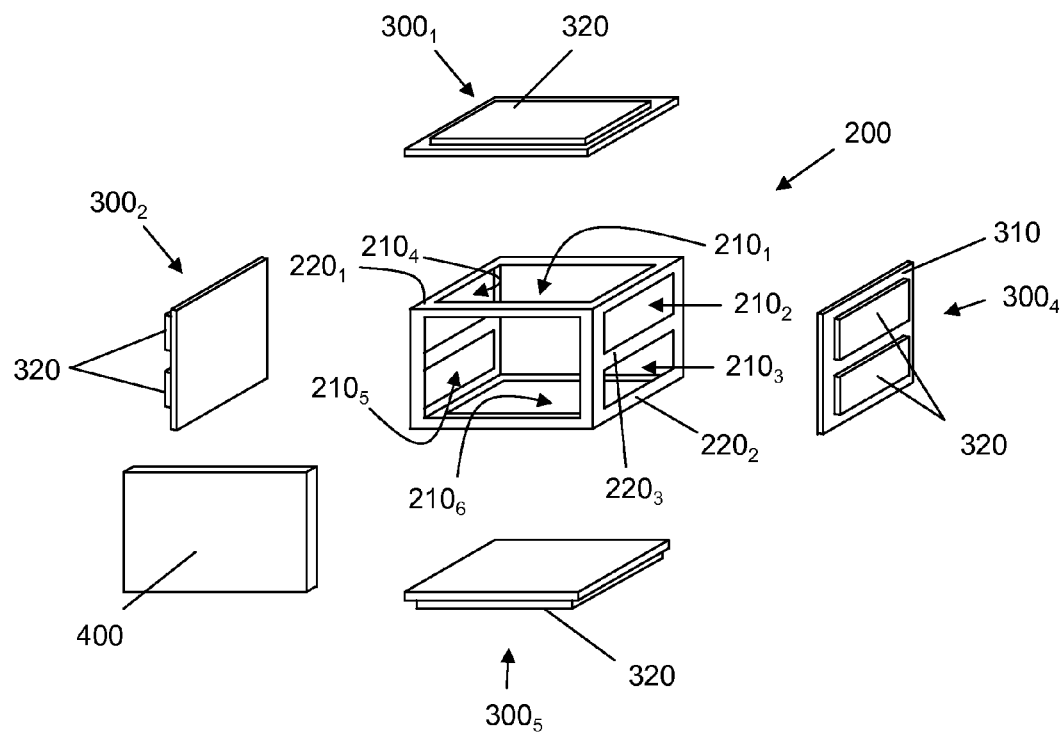
FIGS. 9A-B are schematic perspective views of a representative housing and associated components thereof, including non-conductive members.
Figure 9B:
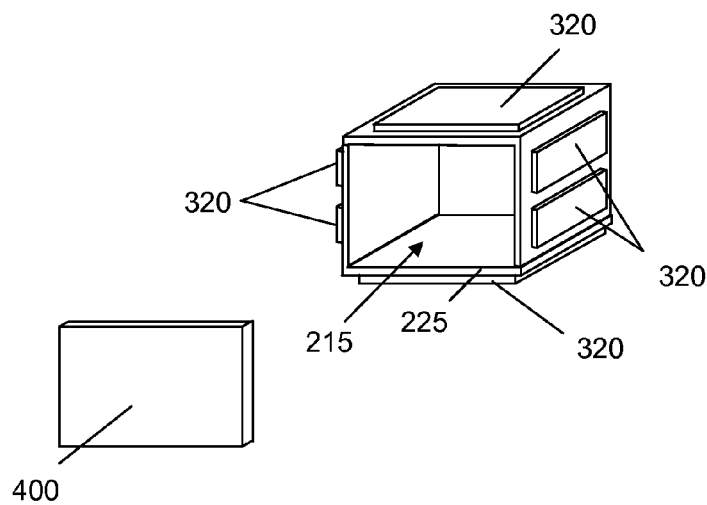

Referring now to FIGS. 9A-B, schematic perspective views of a representative frame 200 and non-conductive members $300 1_{1-5}$ for a housing of an implantable medical device are shown. The frame 200 includes one or more openings $210_{1-6}$. An opening $210_{1-6}$ may be formed by an edge or ridge (e.g., $220_1$, $220_2$, $220_3$) of frame 200. The depicted inserts $300_{1-5}$ contain raised features 320 that are shaped substantially similar to the shape of one or more opening $210_{1-6}$. The depicted non-conductive members $300_{1-5}$ also include a recessed portion 310 configured to sit flush against one or more edge or ridge (e.g., $220_1$, $220_2$, $220_3$) of frame 200. In the depicted embodiment, a recessed portion 310 of a non-conductive member 300 is configured to sit flush against an interior surface of one or more edge or ridge. However, it will be understood that recessed portion 310 of a non-conductive member 300 may be configured to sit flush against an exterior surface of one or more edge or ridge of frame 200. The raised features 320 are inserted through one or more openings of the frame 200 to provide support for thin foil or sheet (not shown in FIGS. 9A-B). Non-conductive members $300_{1-5}$ may be affixed to frame 200 by any suitable mechanism, such as adhesion, interference or snap fit, fastener, overmolded, glassed or brazed or the like. In various embodiments, one or more of the non-conductive members $300_{1-5}$ are molded into the frame 200. Raised features 320 are shown protruding from frame 200 in FIG. 9B for purposes of illustration, but will desirably be flush with exterior surface of frame 200.

Non-conductive members, such as those depicted in FIGS. 9A-B, may be formed of any suitable material. Examples of suitable non-conductive material include polymeric materials such as silicone, polyurethane, polycarbonate, polysulfone, and the like Also glass or ceramic feedthrough insulators. In various embodiments, the non-conductive members are composed of a transparent single-crystal material. The transparent single crystal non-conductive member may be anodically bonded to the frame to form a hermetic seal or may be otherwise bound or attached to the frame. If both metallic foil and underlying transparent single-crystal material form a hermetic seal with the frame, additional assurances that the hermetic seal will be maintained following implant may be gained.

Figure 10A:
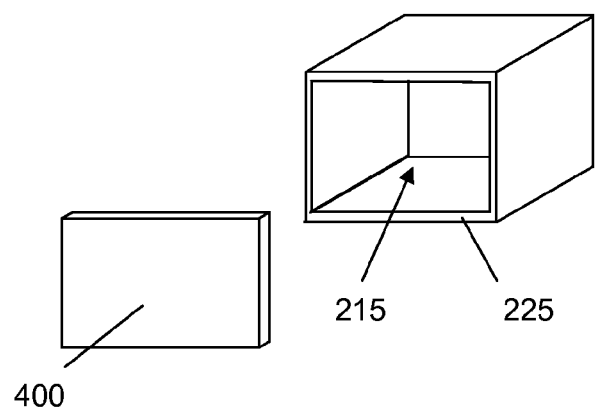
FIG. 10A is a schematic perspective view of a representative housing with an exploded end wall.

As shown in FIGS. 9A-B and FIG. 10A, a housing of an implantable medical device as described herein may include an end wall 400. In the depicted embodiments, the frame of the housing includes an opening 215 formed by a ridge or edge 225. The end wall 400 may be affixed to the frame and contact the ridge or edge 225. For example the end wall 400 may be affixed to the frame via welding, adhesive, fastener, or the like. Prior to affixing the end wall 400 to the frame, internal components of the implantable medical device may be placed into the housing or frame via opening 215. The end wall 400 may be formed of any suitable material or combinations of materials. In various embodiments, the end wall 400 is formed of metallic material, such as a material described above as suitable for use in forming a frame or foil, and may be welded to the ridge or edge 225. In various embodiments, the end wall 400 is formed of non-conductive material such as ceramic or glass with or without a feedthrough extending through it and foil or sheet (not show in FIGS. 9A-B and FIG. 10A) covers the end wall 400 and seals the housing. While an end wall 400 is shown with regard to FIGS. 9A-B and FIG. 10A, it will be understood that an end wall may be readily employed with regard to the embodiments depicted in FIGS. 5-8.

Figure 11:
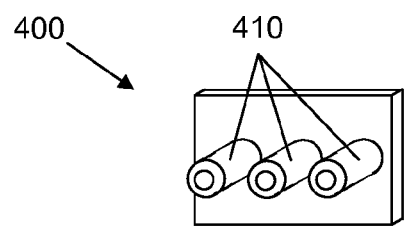
FIG. 11 is a schematic perspective view of an end wall including feedthroughs.

Referring now to FIG. 11, a perspective view of an end wall 400 is shown. One or more feedthroughs 410 extend through end wall 400. The feedthroughs 410 may serve as conduits through which electrical components disposed within the housing may be coupled to electrical components external to the housing. The feedthroughs 410 may be hermetically sealed to prevent fluid from entering the housing when the device is implanted in a subject.

While not shown, it will be understood that frame 200, e.g. as depicted in FIGS. 5-10A may include features that aid in the mechanical structure for alignment of or attachment to other components such as a battery or connector.

Thus, embodiments of HOUSING FOR IMPLANTABLE MEDICAL DEVICE are disclosed. One skilled in the art will appreciate that the housings, devices, systems and methods described herein can be practiced with embodiments other than those disclosed. The disclosed embodiments are presented for purposes of illustration and not limitation.

What is claimed is:

1. An implantable medical device, comprising:
   control electronics;
   a rechargeable battery operably coupled to the control electronics;
   a recharge coil operably coupled to the rechargeable battery; and
   a metallic housing comprising a frame and a metallic foil welded to the frame to hermetically seal the housing, wherein the frame comprises plurality of openings and the foil covers the plurality of openings, wherein the total surface area occupied by the plurality of openings of the frame, relative to the surface area of the housing, is about 75% or greater,
   wherein the control electronics, the rechargeable battery and the recharge coil are disposed in the housing.

2. The implantable medical device of claim 1, wherein the metallic foil is formed from a titanium alloy.

3. The implantable medical device of claim 2, wherein the titanium alloy is selected from the group consisting of a Ti6AI4V alloy, a Ti8AIMo-IV alloy, a Ti6242 alloy, an SP-700 alloy, a Ti5AI2.5Sn alloy, Ti-4Al-2.5V-1.5Fe-0.25O and a Ti3AI2V alloy.

4. The implantable medical device of claim 1, wherein the foil has a thickness of less than 0.007 inches.

5. The implantable medical device of claim 1, wherein the foil has a thickness of less than 0.006 inches.

6. The implantable medical device of claim 1, wherein the foil has a thickness of between about 0.004 inches and about 0.006 inches.

7. The implantable medical device of claim 1, wherein the frame is formed from a titanium alloy.

8. The implantable medical device of claim 1, further comprising a non-conductive member inserted in the opening.

9. The implantable medical device of claim 8, wherein the foil is in contact with the non-conductive member.

10. The implantable medical device of claim 8, wherein the non-conductive member is formed from a polymeric material.

11. The implantable medical source of claim 1, wherein the recharge coil is aligned with the opening.

12. The implantable medical device of claim 1, further comprising a telemetry antenna disposed within the housing, wherein the telemetry antenna is aligned with the opening.

13. The implantable medical device of claim 1, wherein the device is an electrical signal generator.

14. The implantable medical device of claim 1, wherein the device is an infusion device.

15. A method for assembling an implantable medical device, comprising:
- introducing control electronics into a metallic frame of a housing, the frame having a plurality of openings consisting of at least a first plurality of openings and a second opening, wherein the total surface area occupied by the plurality of openings of the frame, relative to the surface area of the housing, is about 75% or greater;
- introducing a rechargeable battery into the metallic frame of the housing;
- introducing a recharge coil into the metallic frame of the housing;
- welding a metallic foil having a thickness of less than 0.007 inches to the frame, such that the foil covers the first plurality of openings;
- welding a metallic end wall to the frame, such that end wall covers the second opening.

16. The method of claim 15, further comprising disposing a non-conductive member in the first opening to provide structural support for the foil.

17. The method of claim 15, wherein the recharge coil is aligned with the first opening.

18. The method of claim 17, further comprising introducing a telemetry antenna into the metallic frame of the housing, wherein the telemetry antenna is aligned with the first opening.

* * * * *